(12) United States Patent
Awtrey

(10) Patent No.: US 12,414,782 B2
(45) Date of Patent: Sep. 16, 2025

(54) TARGETING GUIDE AND METHODS OF USING THE TARGETING GUIDE

(71) Applicant: WRIGHT MEDICAL TECHNOLOGY, INC., Memphis, TN (US)

(72) Inventor: George Matthew Awtrey, Bartlett, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 657 days.

(21) Appl. No.: 17/760,150

(22) PCT Filed: Mar. 24, 2021

(86) PCT No.: PCT/US2021/023812
§ 371 (c)(1),
(2) Date: Aug. 4, 2022

(87) PCT Pub. No.: WO2021/206905
PCT Pub. Date: Oct. 14, 2021

(65) Prior Publication Data
US 2023/0077222 A1 Mar. 9, 2023

Related U.S. Application Data

(60) Provisional application No. 63/007,515, filed on Apr. 9, 2020.

(51) Int. Cl.
*A61B 17/17* (2006.01)
*A61B 17/56* (2006.01)

(52) U.S. Cl.
CPC .... *A61B 17/1775* (2016.11); *A61B 2017/565* (2013.01)

(58) Field of Classification Search
CPC .................. A61B 17/1775; A61B 17/1714
See application file for complete search history.

(56) References Cited

U.S. PATENT DOCUMENTS

| 5,478,341 | A | 12/1995 | Cook et al. |
| 10,342,590 | B2 | 7/2019 | Bays et al. |
| 11,000,327 | B2 | 5/2021 | Schlotterback et al. |
| 2020/0006069 | A1 | 1/2020 | Dewey et al. |

FOREIGN PATENT DOCUMENTS

WO 2018063329 A1 4/2018

OTHER PUBLICATIONS

International Search Report and Written Opinion issued in connection with International Patent Application No. PCT/US2021/023813, Jul. 1, 2021, 10 pages.

*Primary Examiner* — Andrew Yang
(74) *Attorney, Agent, or Firm* — Duane Morris LLP

(57) ABSTRACT

Disclosed are bone screw drill targeting guides and methods for using such targeting guides that are useful in surgical procedures for correcting hallux valgus deformity.

18 Claims, 14 Drawing Sheets

300
(Continued)

(g) translating the metatarsal head portion (B2) in the lateral direction with respect to the metatarsal base portion (B1) by pivoting the targeting guide about the fulcrum (150) while bracing the fulcrum against the lateral side of the metatarsal base portion (B1), whereby the anchoring portion (110) urges against the metatarsal head portion (B2) — 307

(h) holding the metatarsal head portion (B2) in the translated position by affixing the targeting guide (100) to the metatarsal base portion (B1) by placing a fixation pin through a hole (122) the is located in the body (120) between the fulcrum (150) and the curved portion (120C) — 308

(i) inserting a first guide wire (W1) through the guide hole (135a) in the targeting portion (130) — 309

(j) adjusting the position of the targeting portion (130) along the curved portion (120C) until the first guide wire (W1) is identifying a desired trajectory for a bone screw to be driven trough the metatarsal base portion (B1) and into the metatarsal head portion (B2) — 310

FIG. 13

TARGETING GUIDE AND METHODS OF USING THE TARGETING GUIDE

CROSS-REFERENCE TO RELATED APPLICATIONS

This application is a National Stage Application, filed under 35 U.S.C. 371, of International Patent Application No. PCT/U.S.2021/023812, filed on Mar. 24, 2021, which claims priority to United Stated provisional Application No. 63/007,515, filed Apr. 9, 2020, the entire disclosures of which are incorporated herein by reference.

FIELD OF DISCLOSURE

The present disclosure relates to bone screw drill targeting guides that can be used in surgical procedures for correcting hallux valgus deformity.

BACKGROUND

During a minimally invasive Chevron and Akin osteotomy (MICA) procedure for correcting hallux valgus deformity, a Chevron osteotomy is made in the first metatarsal bone separating the head portion of the first metatarsal from the remainder of the metatarsal. The metatarsal head is then shifted laterally and fixed with two screws. K-wires are traditionally used to hold the metatarsal head at the intended translated position during the subsequent pre-drilling for screws and screw fixation procedure. Thus, the trajectory of the K-wires through the metatarsal shaft and the shifted metatarsal head need to be accurate. Achieving the desired k-wire trajectory can be difficult. Therefore, a guiding instrument for setting the trajectory of the k-wire is desired.

SUMMARY

Present disclosure provides a targeting guide that comprises: an anchoring portion comprising at least one guide hole configured for receiving an anchoring element; a targeting portion; a fulcrum; and a body connecting the anchoring portion, the targeting portion, and the fulcrum, wherein, the anchoring portion, the targeting portion, and the fulcrum all extend from the body in a first direction, the fulcrum is located on the body between the anchoring portion and the targeting portion, the body is shaped so that the fulcrum is not in line with the anchoring portion and the targeting portion, the positions of the anchoring portion and the fulcrum on the body are fixed, the body has a curved section whose curvature is defined by a circular arc with a radius of curvature and the targeting portion is slidably connected to the body and is configured to slide along the curved section between a first position and a second position, the radius of curvature has its center located at a point between the anchoring portion and the fulcrum and an axis going through the center of the radius of curvature defines a rotational axis for the targeting portion sliding along the curved section, the targeting portion comprises at least one targeting hole provided on the side of the targeting portion that is extending from the body in the first direction, wherein the targeting hole is oriented so that its longitudinal axis is generally oriented toward the rotational axis.

A method of using any one of the targeting guide embodiments disclosed herein is also disclosed.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

FIGS. 12-13 show a flowchart for the method of using the targeting guide 100 according to an aspect of the present disclosure.

DETAILED DESCRIPTION

Figure 1:
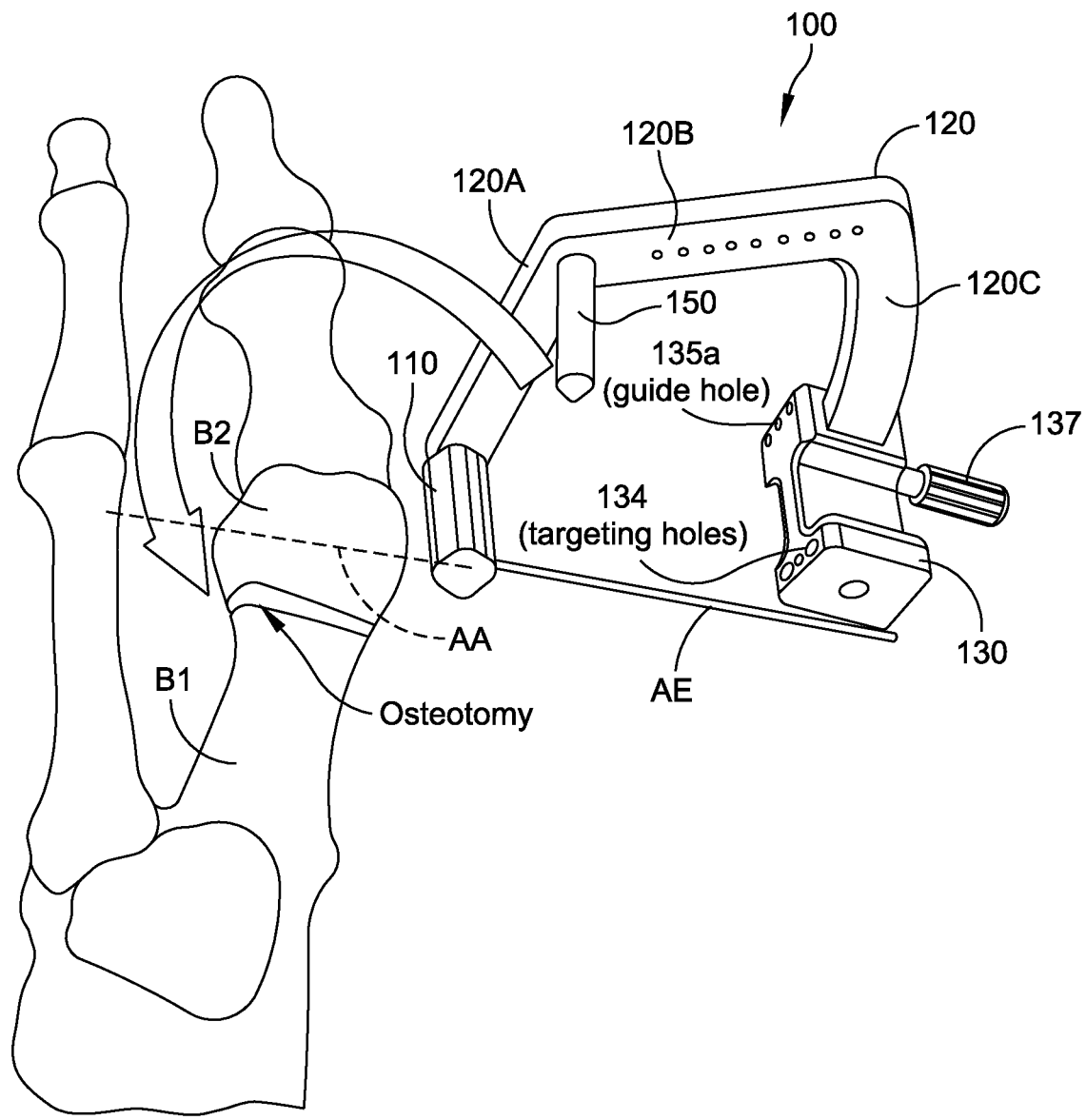
FIG. 1 is an illustration showing the targeting guide 100 according to an embodiment along with a skeletal foot. The anchoring portion 110 of the targeting guide 100 is slipped over an anchoring element AE that has been placed from the medial side of a metatarsal head portion B2 in the lateral direction. In the Figure, a rubber band is shown holding the metatarsal head portion B2 together with the rest of the foot which is being used just for illustration purposes and it is not part of the targeting guide 100.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Referring to FIGS. 1-6, a targeting guide 100 is disclosed for placing guide-wires G1, G2 through two portions of a bone after a first metatarsal bone has been cut into a first bone portion B1 and a second bone portion B2 is disclosed. The targeting guide 100 comprises an anchoring portion 110, a targeting portion 130, a fulcrum 150, and a body 120 connecting the anchoring portion 110, the targeting portion 130, and the fulcrum 150.

The body 120 has three sections: a first section 120A which extends from the end where the anchoring portion 110 is to where the fulcrum 150 is attached; a second section 120B; and a third curved section 120C to which the targeting portion 130 is slidably attached.

The anchoring portion 110 comprises at least one guide hole 112 configured for receiving an anchoring element AE. An example of the anchoring element AE is an olive wire. The anchoring portion 110, the targeting portion 130, and the fulcrum 150 all extend from the body 120 in a first direction noted by the arrow FD in FIGS. 6A and 7. The body 120 is shaped so that the fulcrum 150 is not in line with the anchoring portion 110 and the targeting portion 130. As shown, the body 120 has a "C" shaped configuration. The fulcrum 150 is located on the body 120 between the anchoring portion 110 and the targeting portion 130. The positions of the anchoring portion 110 and the fulcrum 150 on the body 120 are fixed.

Figure 3B:
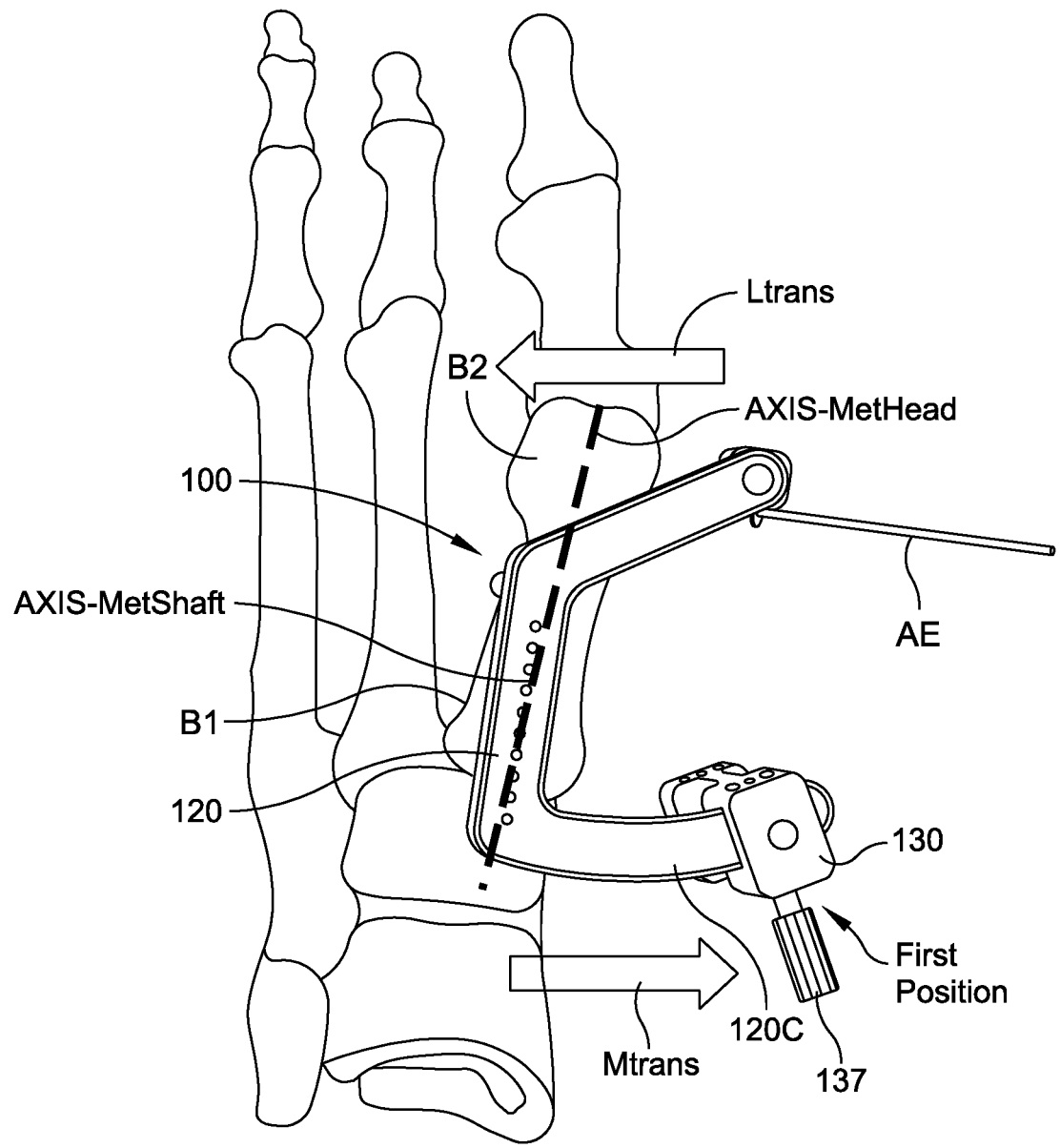
FIG. 3B is an illustration showing a view from the dorsal side of the skeletal foot with the targeting guide 100 from FIG. 1 that has now been rotated about the anchoring element AE so that the targeting guide 100 is in position on the dorsal side of the skeletal foot. In this view the metatarsal head B2 and the FIG. 4. is the arrangement shown in FIG. 3B where the metatarsal head portion B2 has been translated laterally using the targeting guide 100 and the targeting portion 130 is in its first position.
Figure 4:
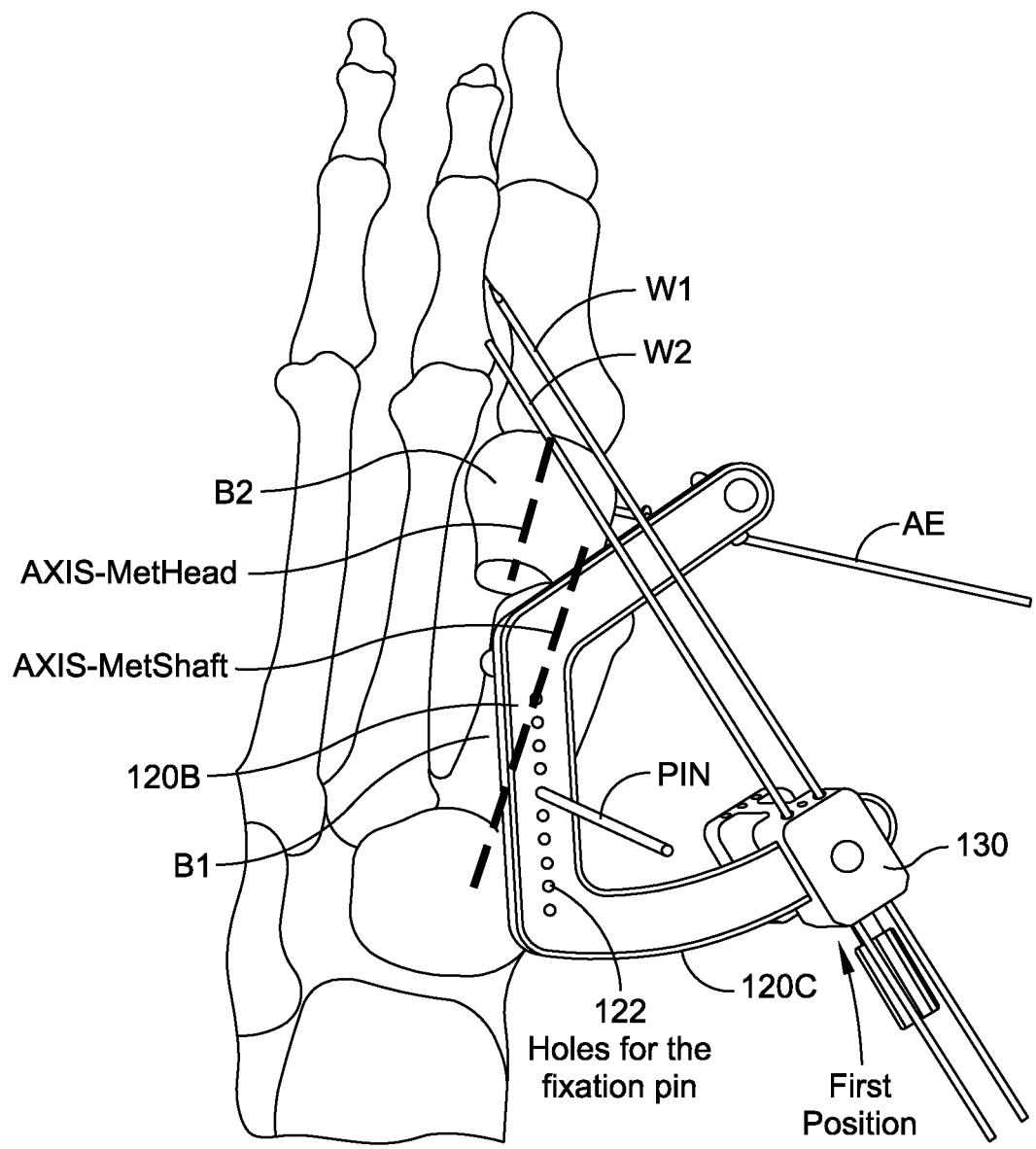
Figure 5:
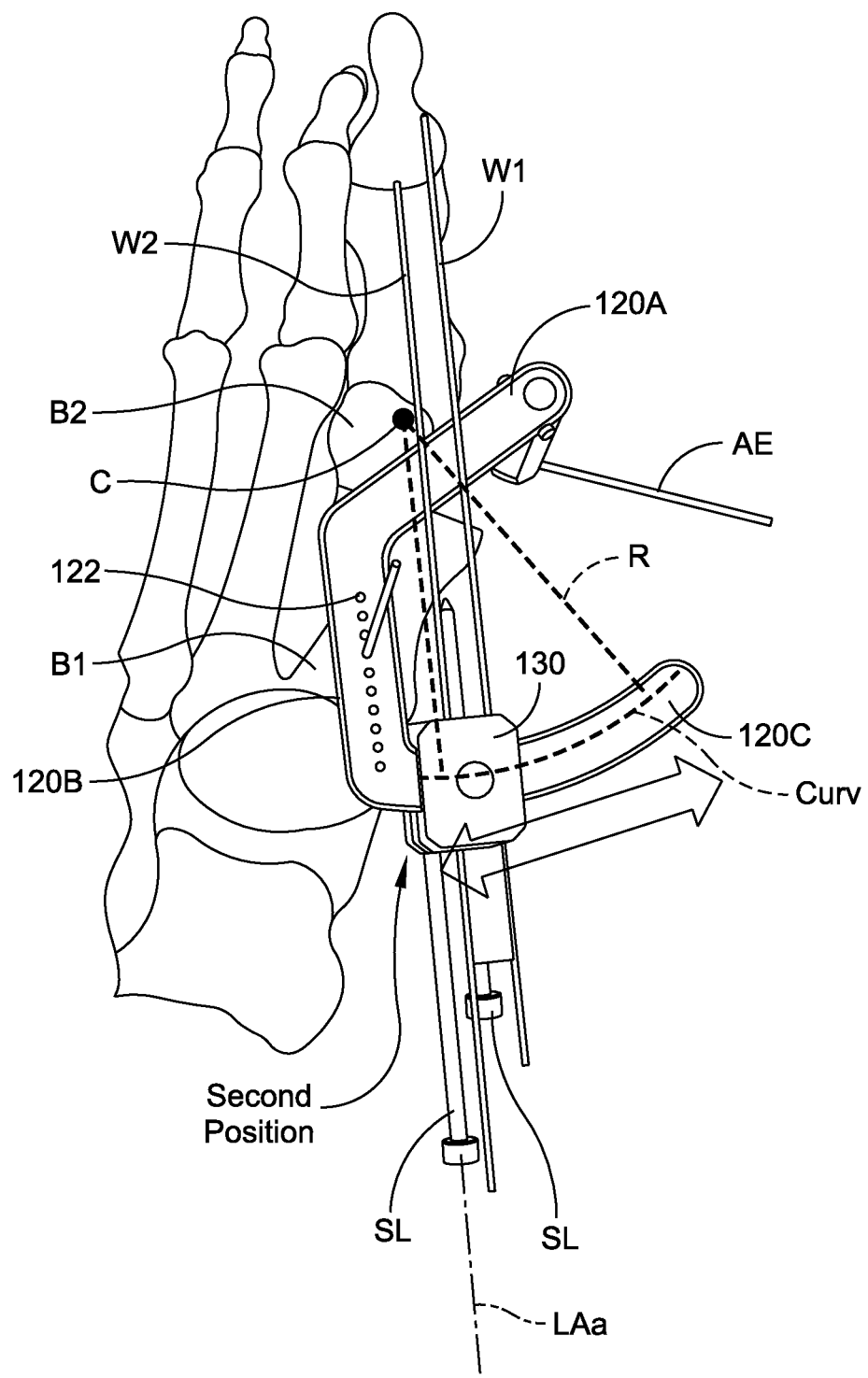
FIG. 5 is another view of the arrangement in FIG. 4 but with the targeting portion 130 in its second position.
Figure 8:
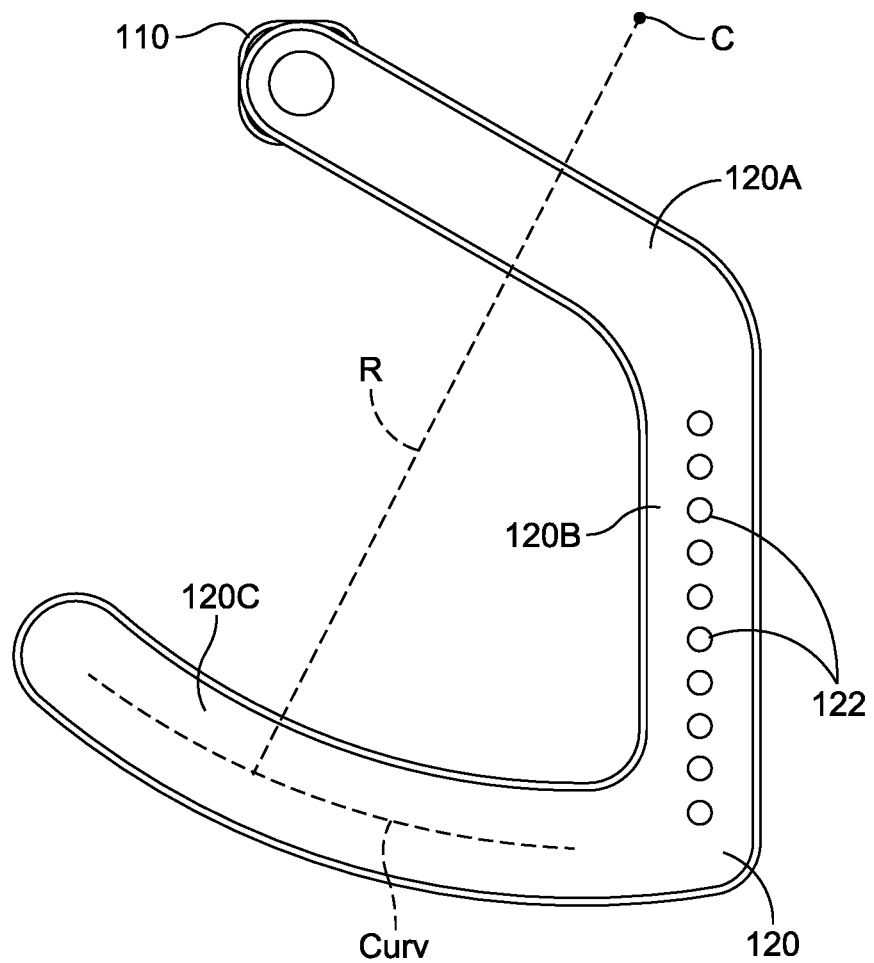
FIG. 8 is a top view of the body portion 120 of the targeting guide 100.

Referring to FIGS. 5 and 8, the body 120 has a curved section 120C whose curvature is defined by a circular arc Curv with a radius of curvature R. The targeting portion 130 is slidably connected to the curved section 120C of the body 120. The targeting portion 130 is configured to slide along the curved section 120C between a first position shown in FIG. 3B and a second position shown in FIG. 5. The two positions are at the two ends of the curved section 120C. As shown in FIGS. 5, 8, and 9B, the radius of curvature R of the circular arc Curv has its center C located at a point beyond the guide body. Thus, the center C is a fixed point in space in the targeting guide's frame of reference. The location of the center C for a given targeting guide 100 is designed to be located in an area approximately centered within the metatarsal head B2 when the targeting guide 100 is in the position as shown in FIGS. 4 and 5 where the targeting guide 100 has laterally translated the metatarsal head B2 to a desired position. An axis going through the center C of the radius of curvature defines a rotational axis RA for the targeting portion 130 sliding along the curved section 120C. The rotational axis RA is identified in FIG. 9B.

The targeting portion 130 comprises at least one targeting hole 134 provided on the side of the targeting portion 130 that is extending from the curved section 120C of the body 120 in the first direction. The at least one targeting hole 134 extends through the targeting portion 130 along a direction so that its longitudinal axis LAa is generally oriented toward the rotational axis RA.

In some embodiments, the at least one targeting hole 134 is sized to receive a drill guide sleeve SL or a guide wire.

In some embodiments, the targeting portion 130 comprises two targeting holes 134 provided on the side of the targeting portion where both targeting holes 134 extend from the body 120 in the first direction. The second targeting hole 134 also extends through the targeting portion 130 along the same direction as the first targeting hole so that the longitudinal axis LAb of the second targeting hole 134 is parallel to the longitudinal axis LAa of the first targeting hole 134.

In some embodiments, the second targeting hole 134 is also sized to receive a drill guide sleeve SL or a guide wire.

In some embodiments, the targeting portion 130 further comprises at least one guide hole 135 spaced apart from the at least one targeting hole 134. The at least one guide hole 135 extends through the targeting portion 130 in a direction parallel to the at least one targeting hole 134. As will be described below referring to the flowchart 300 of FIGS. 12-13, during the method of using the targeting guide 100, the guide holes 135 can be used for the guide wires W1 that hover over the patient's foot for aligning using fluoroscopy.

Referring to FIGS. 4 through 6B, at least one guide hole 135 is configured to receive a guide wire W1.

The anchoring portion 110 comprises a guide hole 112 that is oriented so that the longitudinal axis AA of the guide hole 112 is orthogonal to the rotational axis RA. The anchoring portion 110 is connected to the body 120 by a swiveling joint J configured so that as the anchoring portion 110 swivels, the longitudinal axis AA of the guide hole 112 stays parallel to a plane defined by the longitudinal axis LAa of the targeting hole 134. The plane P is defined by the sweeping motion of the longitudinal axis LAa as the targeting portion 130 slides along the curved section 120C. In the embodiments where the targeting portion 130 comprises two targeting holes 134, the plane P is defined by the sweeping motion of the longitudinal axes LAa and LAb of the two targeting holes 134 as the targeting portion 130 slides along the curved section 120C. (See FIG. 9B)

As can be seen in FIGS. 1, 4, 5, 7, and 8, for example, in some embodiments, the body 120 further comprises a plurality of holes 122 provided between the fulcrum 150 and the curved section 120C. The holes 122 are oriented generally in the first direction, wherein the holes 122 are configured for receiving fixation pins. As shown in FIG. 5, one or more fixation pins PIN can be placed through one or more of the holes 122 and driven into the metatarsal shaft B1 to hold the translated position of the metatarsal shaft B1 and metatarsal head B2 against the targeting guide 100 so that the targeting operation with the targeting portion 130 can be carried out.

Figure 12:
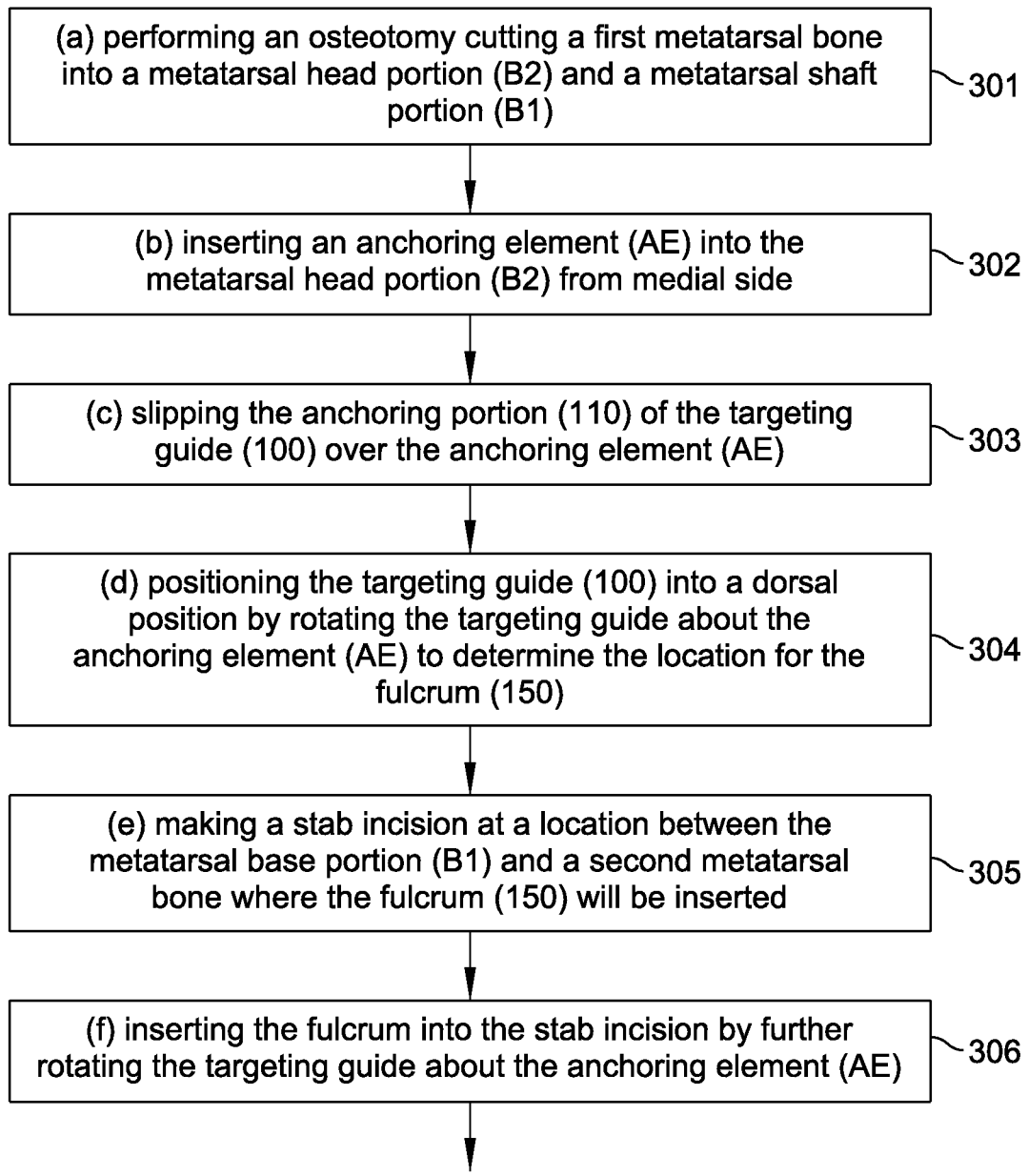

Referring to the flowchart 300 in FIGS. 12-13, a method of using the targeting guide 100 for hallux valgus correction procedure, for example, is disclosed. The method comprises (a) performing an osteotomy cutting a first metatarsal bone into a metatarsal head portion B2 and a metatarsal shaft portion B1. (See Box 301). The osteotomy cut can be a Chevron or a straight cut.

Figure 2:
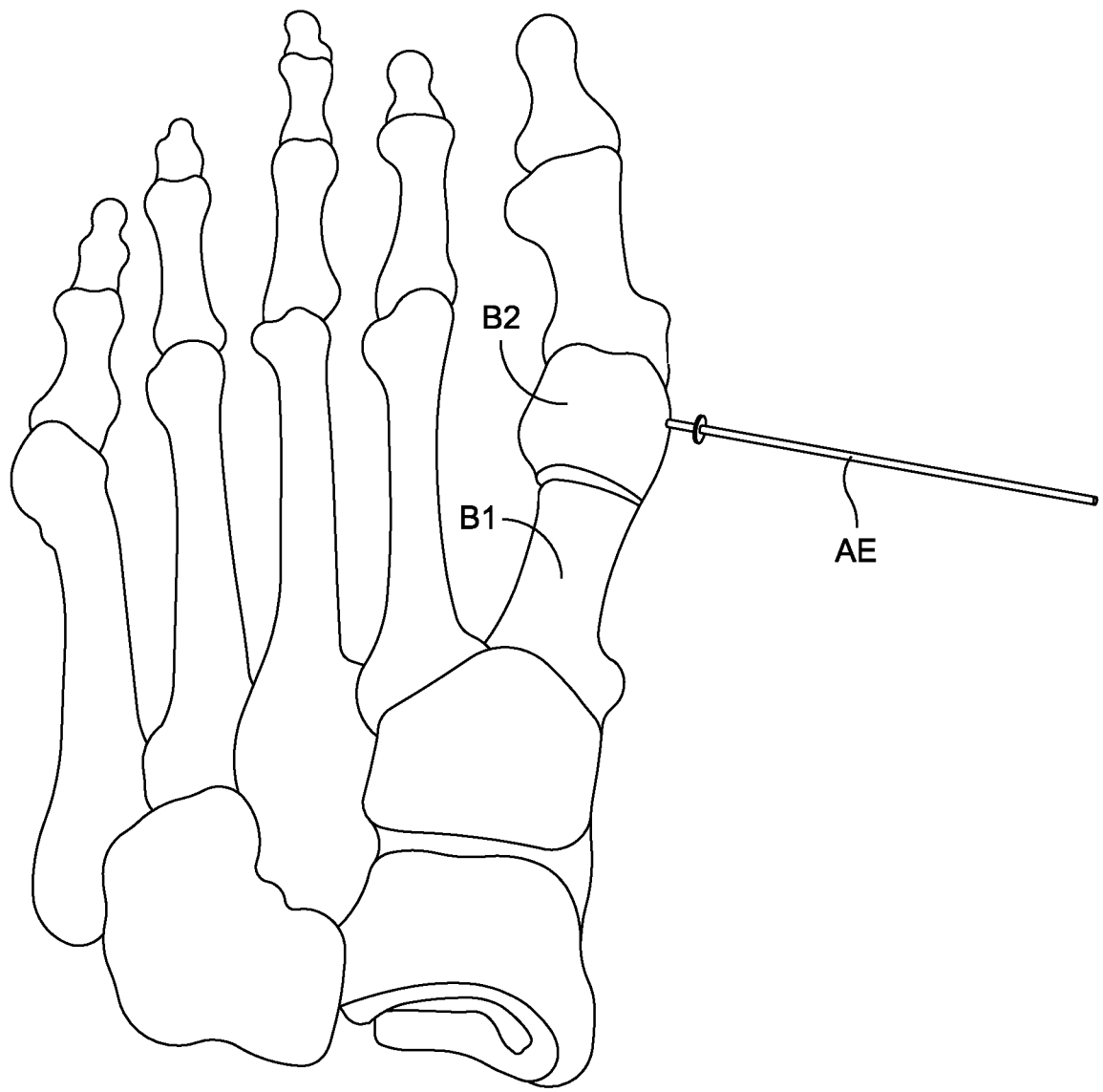
FIG. 2 is an illustration showing the anchoring element AE that has been placed from the medial side of a metatarsal head portion B2 in the lateral direction according to the method disclosed herein.

Next, (b) an anchoring element AE is inserted into the metatarsal head portion B2 from the medial side. (See Box 302). The anchoring element AE can be fixation pins, K-wires, olive wires. FIG. 2 shows an olive wire as the anchoring element AE that is inserted into the metatarsal head portion B2 from the medial side.

Figure 3A:
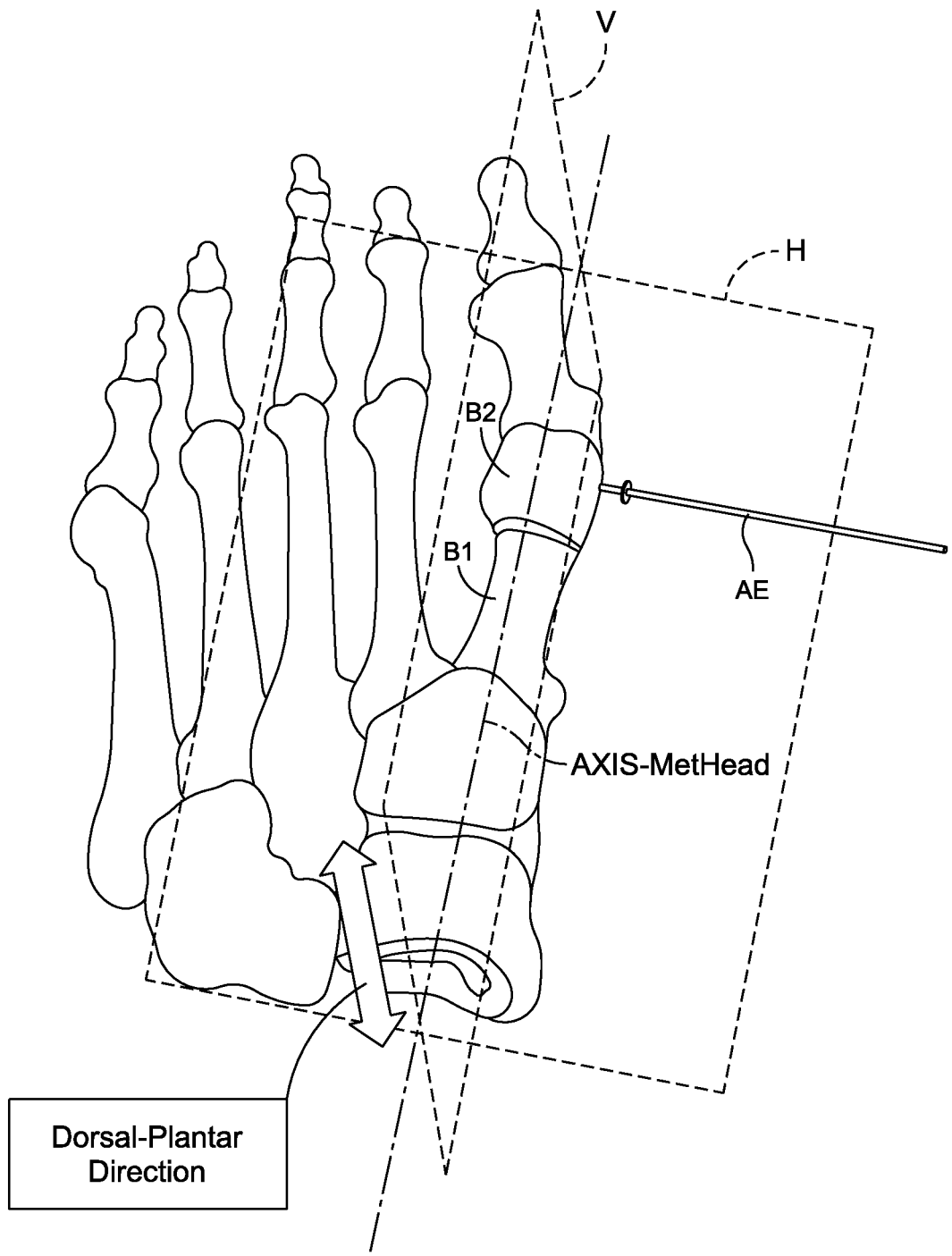
FIG. 3A is an illustration showing the preferred geometric relationship between the placement of the anchoring element AE and the metatarsal head portion B2.

The anchoring element AE is preferably placed into the metatarsal head portion B2 so that the anchoring element AE goes through as close to the geometric center of the metatarsal head portion B2 as possible and be orthogonal to the longitudinal axis Axis-MetHead of the metatarsal head portion B2. This will enable the targeting guide 100 to be in the proper position when it is in the configuration shown in FIGS. 4 and 5 and the center C of the radius of curvature for the circular arc Curv is at the proper location and the trajectory of the targeting holes 134 represented by their longitudinal axis LAa will be aimed toward the geometric center of the metatarsal head B2. Referring to FIG. 3A, additionally, the anchoring element AE is preferably placed and oriented so that the anchoring element AE lies in the plane H that is orthogonal to the vertical plane V (i.e., the plane that is oriented in dorsal-plantar direction) that contains the longitudinal axis Axis-MetHead of the metatarsal head portion B2, where the plane H also contains the longitudinal axis Axis-MetHead. In other words, the longitudinal axis Axis-MetHead is preferably at the intersection of the two planes H and V.

Next, (c) the anchoring portion 110 of the targeting guide 100 is slipped over the anchoring element AE. (See Box 303). This arrangement can be seen in FIG. 1.

Next, (d) the targeting guide 100 is positioned into a dorsal position by rotating the targeting guide about the anchoring element AE to determine the location for the fulcrum 150. (See Box 304). The fulcrum 150 is to be inserted into the foot from the dorsal side between the first metatarsal and the second metatarsal.

Next, (e) a stab incision is made at a location between the metatarsal shaft portion B1 of the first metatarsal and the second metatarsal bone where the fulcrum 150 will be inserted. (See Box 305).

Next, (f) the fulcrum is inserted into the stab incision by further rotating the targeting guide about the anchoring element AE. (See Box 306). The arrangement of the targeting guide 100 after this step (f) is shown in FIG. 3B. At this point, the metatarsal head portion B2 and the metatarsal shaft portion B1 are still in their natural position. The longitudinal axis of the metatarsal head portion Axis-MetHead and the longitudinal axis of the metatarsal shaft portion Axis-MedShaft are still in alignment so in FIG. 3B they are seen as being overlapped with each other.

Next, (g) the metatarsal head portion B2 is translated in the lateral direction with respect to the metatarsal base portion B1 by pivoting the targeting guide about the fulcrum 150 while bracing the fulcrum against the lateral side of the metatarsal base portion B1, whereby the anchoring portion 110 urges the metatarsal head portion B2 in the direction indicated by the arrow Ltrans and the fulcrum 150 urges the metatarsal shaft portion B1 in the opposite direction indicated by the arrow Mtrans indicated in FIG. 3B (See Box 307). The translated arrangement of the bones is shown in FIG. 4. In FIG. 4, the Axis-MetHead of the metatarsal head portion B2 and the Axis-MetShaft of the metatarsal shaft portion B1 are no longer in alignment but offset by the translation of the metatarsal head portion B2.

Next, (h) the metatarsal head portion B2 is held in the translated position by affixing the targeting guide 100 to the metatarsal base portion B1 by placing one or more fixation pins PIN through one or more of the holes 122 that are provided in the second section 120B of the body 120 between the fulcrum 150 and the curved section 120C and driven into the metatarsal shaft portion B1. (See Box 308). In the illustrated example shown in FIGS. 4 and 5, one fixation PIN is placed through one of the holes 122. The pin holds the targeting guide 100 and the two bone portions B1, B2 in the configuration shown and enables the next procedural steps for targeting the trajectories for the bone screws that will fix the translated configuration of the two bone portions B1, B2.

Next, (i) a first guide wire W1 is inserted through one of the guide holes 135 in the targeting portion 130 for visualizing the trajectory for a bone screw to be placed through the two bone portions B1, B2. (See Box 309). Optionally, a second guide wire W2 can also be inserted through another of the guide holes 135 that can be used for visualizing the trajectory for a second bone screw to be placed through the two bone portions B1, B2. This arrangement can be seen in FIGS. 4 and 5.

Next, (j) the position of the targeting portion 130 is adjusted along the curved section 120C until the first guide wire W1 is identifying a desired trajectory for a bone screw to be driven through the metatarsal base portion B1 and into the metatarsal head portion B2. (See Box 310).

Figure 9A:
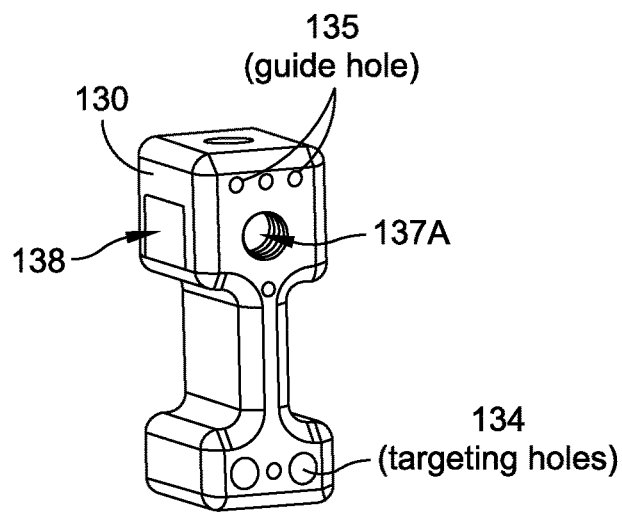
FIG. 9A is a detailed view of the targeting portion 130 of the targeting guide 100.
Figure 9B:
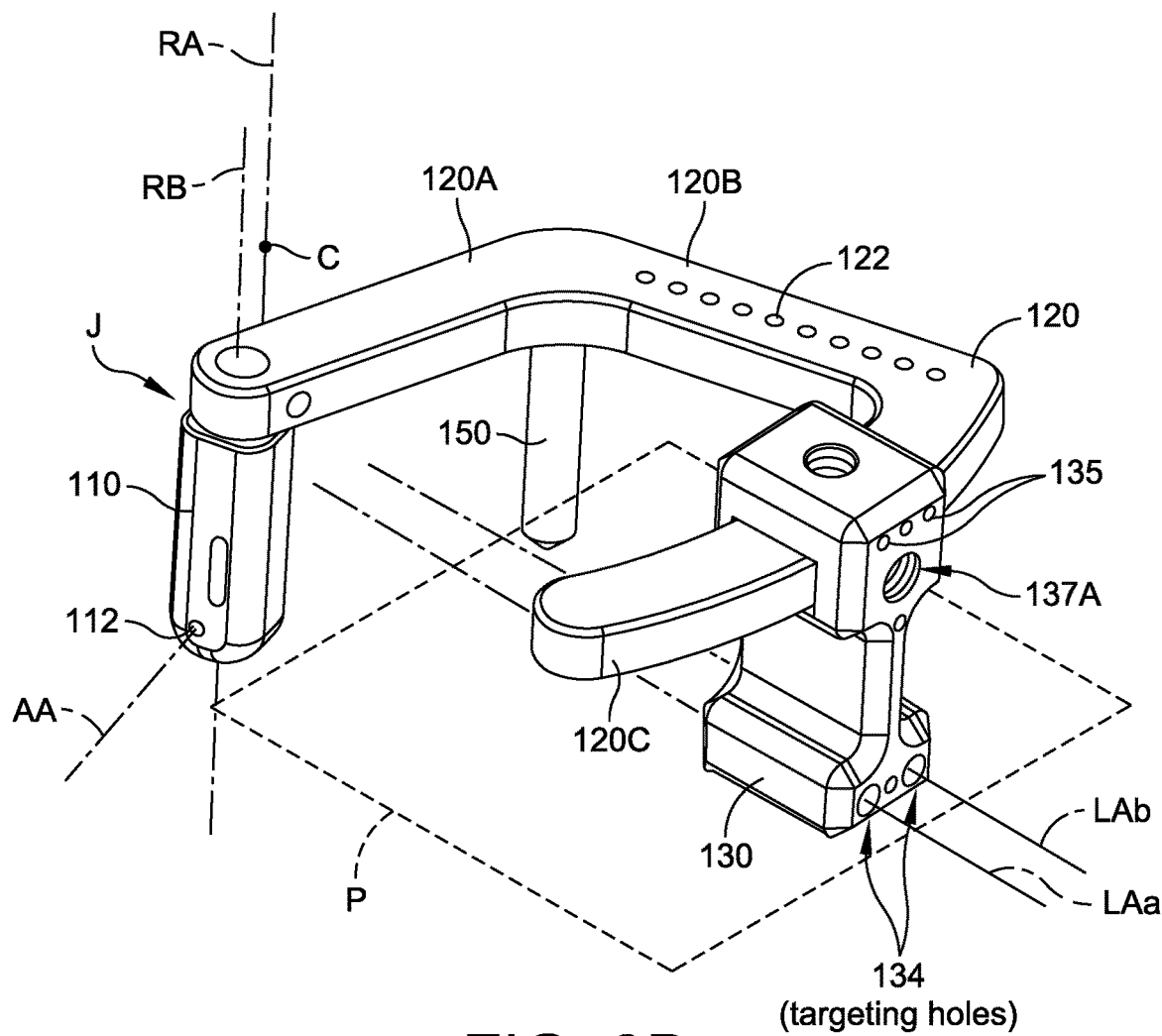
FIG. 9B is a perspective view of the body portion 120 with the targeting portion 130 engaged on the curved section 120C.
Figure 10A:
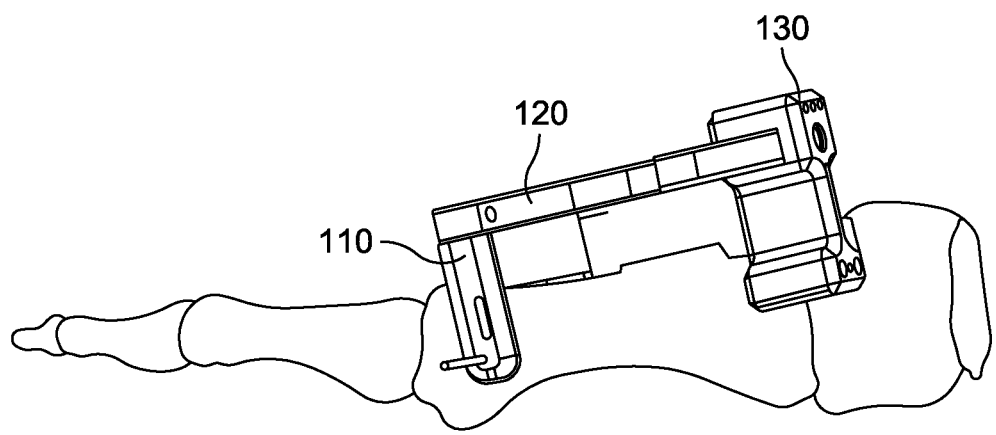
FIGS. 10A-11 are different views of the arrangement shown in FIG. 3B.
Figure 10B:
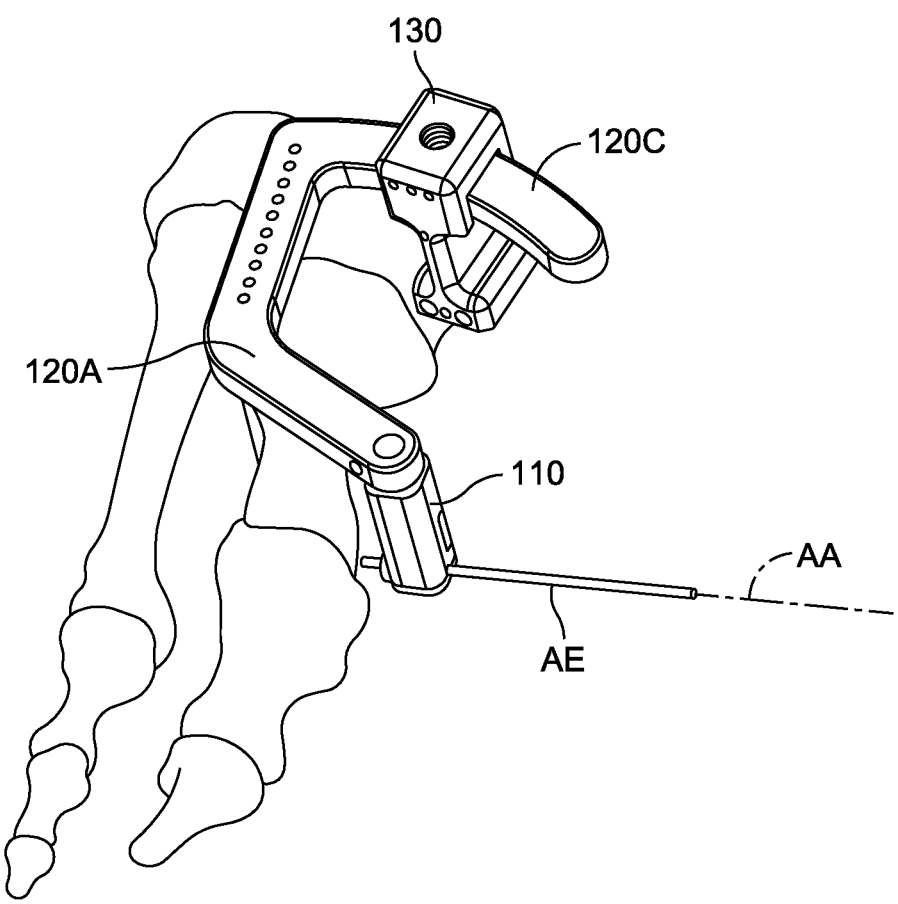
Figure 11:
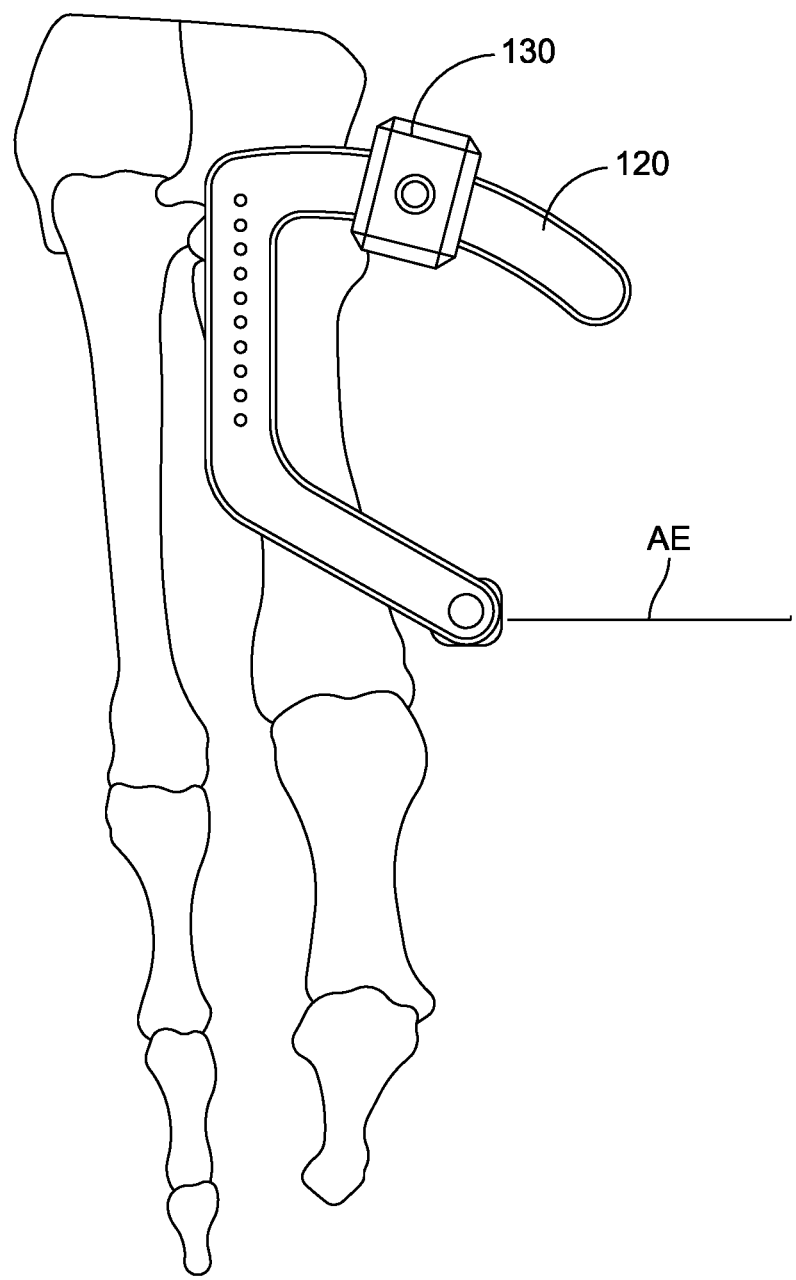

As can be seen in FIGS. 9A and 9B, the guide holes 135 and the targeting holes 134 are vertically spaced apart on the targeting portion 130. The guide holes 135 are located on the targeting portion 130 above the body 120 and the targeting holes 134 are located on the targeting portion 130 below the body 120. The part of the targeting portion 130 that has the targeting holes 134 extends away from the body 120 in the first direction FD (see FIGS. 6 and 7) by a predetermined distance so that when the targeting guide 100 in in position shown in FIG. 5, the guide wires W1 and W2 placed through the guide holes 135 hover over the patient's foot on the dorsal side and the longitudinal axis T of the targeting holes 134 are near and in the vicinity of the longitudinal axis of the metatarsal shaft Axis-MetShaft in the dorsal-plantar direction. This can be seen in the side view of the arrangement of FIG. 5 shown in FIGS. 6A and 6B.

The guide holes 135 and the targeting holes 134 are parallel to each other. More specifically, their longitudinal axes are parallel to each other so that when viewed from the dorsal side as in FIGS. 4 and 5, the guide wires W1 and W2 placed through the guide holes 135 represent the trajectory of the longitudinal axes of the targeting holes 134. That also means that the guide wires W1 and W2 represent the trajectory of the bone screw holes that would be drilled into the bone portions using the targeting holes 134 as guides. Thus, with the guide wires W1 and/or W2 in place, the surgeon can use the guide wires W1 and/or W2 to check the alignment of the trajectory of the targeting holes 134 under fluoroscopy to determine the proper trajectory where the bone screws should be placed to fix the two bone portions B1, B2.

In adjusting the position of the targeting portion 130, the targeting portion 130 is moved between its first position near the terminal end of the curved section 120C of the body 120 (shown in FIG. 4) and its second position near the opposite end of the curved section 120C (shown in FIG. 5). A desired position would be somewhere between those two positions.

Figure 6A:
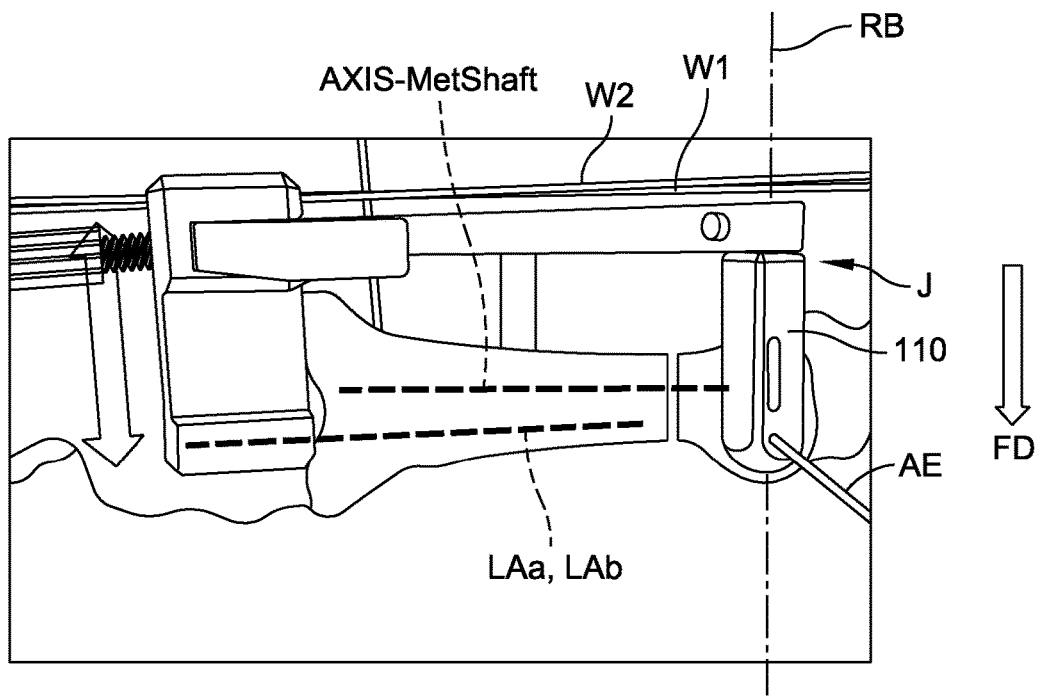
FIGS. 6A and 6B are side view illustrations of the targeting guide arrangement of FIGS. 4 and 5.
Figure 6B:
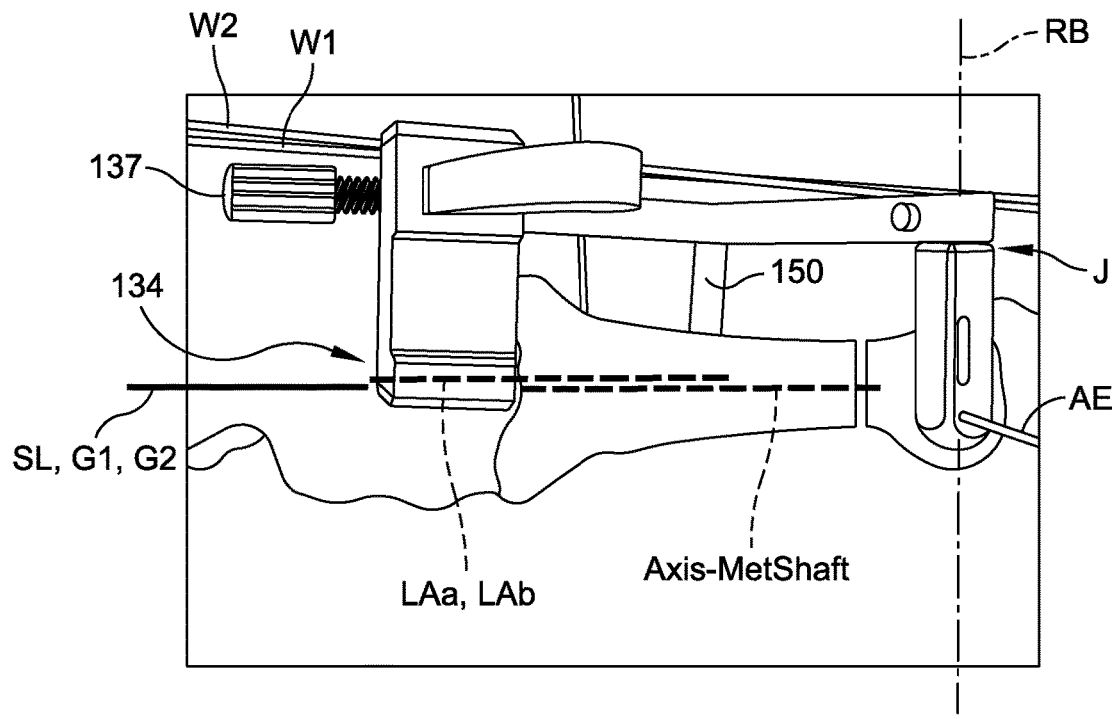
Figure 7:
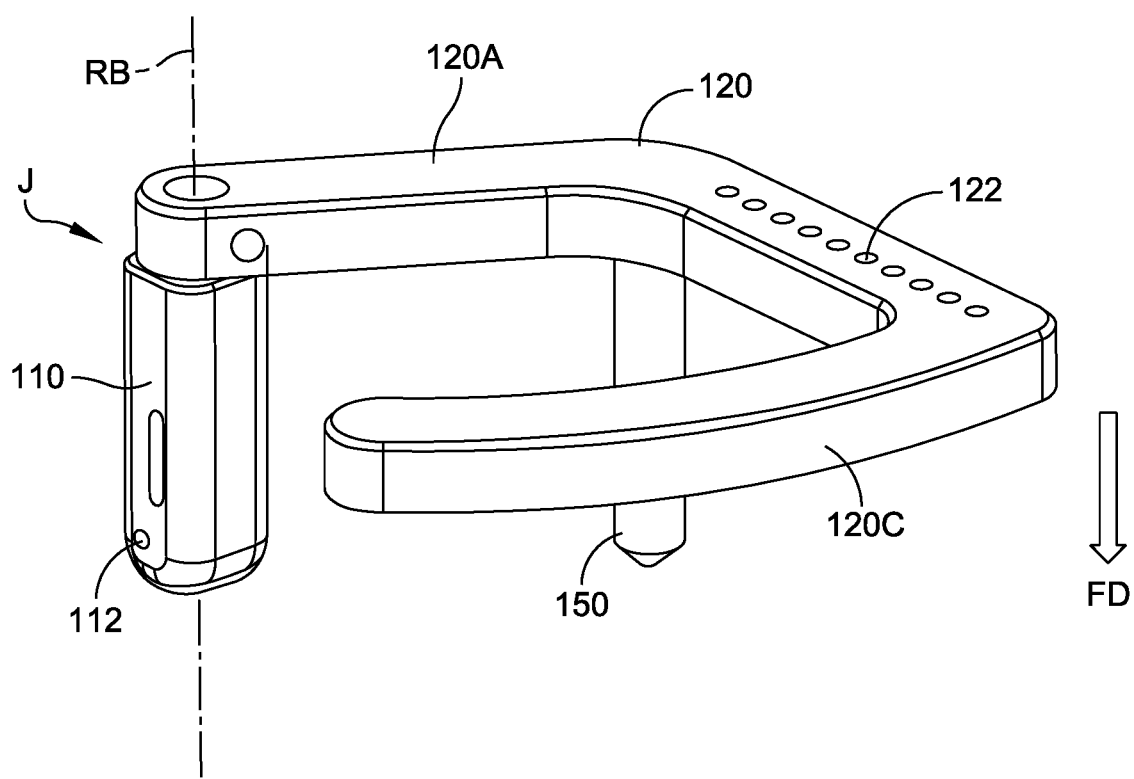
FIG. 7 is a perspective view illustration of the body portion 120 of the targeting guide 100.

The surgeon can also determine the proper trajectory T of the targeting holes 134 in the dorsal-plantar direction by viewing the targeting guide 100 arrangement from the side. The side views are shown in FIGS. 6A and 6B. In FIG. 6A, the trajectory T of the targeting holes 134 is not in line with the longitudinal axis (or the midline) of the metatarsal shaft Axis-MetShaft. At this point, because the anchoring portion 110 of the targeting guide 100 can rotate about the anchoring element AE, the targeting guide 100 can be rotated up or down about the anchoring element AE to align the trajectory T of the targeting holes 134 with the longitudinal axis Axis-MetShaft of the metatarsal shaft. FIG. 6A shows the aligned configuration. In one embodiment, the anchoring portion 110 can rotate around the anchoring axis RB while maintaining a positional distance from the fulcrum 150 relative to the body 120.

Once the trajectory for the bone screws are determined using the targeting portion 130, the holes for the bone screws can be drilled into the two bone portions B1, B2 using the targeting guide 100. However, it is desirable to lock the position of the targeting portion 130 on the curved section 120C to facilitate the subsequent drilling operation. To accomplish this, the targeting portion 130 can be provided with a threaded hole 137A (See FIGS. 9A, 9B) and a locking thumb screw 137 (See FIGS. 1, 6A) that threads through the threaded hole 137A and presses against the curved section 120C that passes through a sliding channel 138 (See FIG. 9A) in the targeting portion 130 and lock the position of the targeting portion 130 on the curved section 120C.

With the targeting guide 100 locked down in the aligned configuration, the method of flowchart 300 can further comprise the step (k) of inserting a drill guide sleeve SL into each of the targeting hole 134 in the targeting portion 130 until the drill guide sleeve SL contacts the patient's skin next to the metatarsal base portion B1 and drilling through the metatarsal base portion B1 and the metatarsal head portion B2 guided by the drill guide sleeve SL. Two drill guide sleeves SL inserted into each of the targeting hole 134 are shown in FIG. 5. Using the drill guide sleeves SL in place the surgeon can drill holes for the bone screws through the two bone portions B1, B2 from the metatarsal shaft portion B1.

Alternatively, rather than using drill guide sleeves SL, guide wires G1, G2 can be inserted through the targeting holes 134 and driven into the bones B1, B2. Then a cannulated drill bit can be slipped over the guide wires G1, G2 to drill into the bones B1, B2 to make holes for bone screws.

In some embodiments of the method of flowchart 300, the step (j) can include identifying the desired trajectory for a bone screw comprises checking the orientation of the first guide wire W1 under a fluoroscope. Then, the step (k) can be carried out.

In some embodiments of the method of flowchart 300, the method can further comprise the step (1) of inserting a drill guide sleeve SL into each of the targeting hole 134 in the targeting portion 130 until the drill guide sleeve SL contacts the patient's skin next to the metatarsal base portion B1 and driving a guide wire through the metatarsal base portion B1 and the metatarsal head portion B2 and using a cannulated drill bit to drill through the metatarsal base portion B1 and the metatarsal head portion B2 guided by the guide wire.

In some embodiments of the method of flowchart 300, the step (j) can include identifying the desired trajectory for a bone screw comprises checking the orientation of the first guide wire W1 under a fluoroscope, then, the step (1) can be carried out.

In some embodiments of the method of flowchart 300, in step (b), the anchoring element AE is inserted into the metatarsal head portion so that the tip of the anchoring element is in the center of the metatarsal head portion. In one preferable embodiment, the anchoring element AE is an olive wire.

In some embodiments of the method of the flowchart 300 further comprises, after step (i) but before step (j), adjusting the targeting guide's position in dorsal-plantar directions to align the longitudinal axis LAa of the targeting hole 134 to the longitudinal axis of the metatarsal base portion B1.

In some embodiments of the method of the flowchart 300, after step (h) but before step (i), further comprises adjusting the targeting guide's position in dorsal-plantar directions to align the longitudinal axis LAa of the targeting hole 134 to the longitudinal axis of the metatarsal base portion B1.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

I claim:

1. A targeting guide comprising:
    an anchoring portion comprising at least one guide hole configured for receiving an anchoring element;
    a targeting portion;
    a fulcrum; and
    a body connecting the anchoring portion, the targeting portion, and the fulcrum,
    wherein,
        the anchoring portion, the targeting portion, and the fulcrum all extend from the body in a first direction,
        the fulcrum is located on the body between the anchoring portion and the targeting portion,
        the body is shaped so that the fulcrum is not in line with the anchoring portion and the targeting portion,
        the positions of the anchoring portion and the fulcrum on the body are fixed,
        the body has a curved section whose curvature is defined by a circular arc with a radius of curvature and the targeting portion is slidably connected to the body and is configured to slide along the curved section between a first position and a second position,
        the radius of curvature has its center located at a point between the anchoring portion and the fulcrum and an axis going through the center of the radius of curvature defines a rotational axis for the targeting portion sliding along the curved section,
        the targeting portion comprises at least one targeting hole provided on the side of the targeting portion that is extending from the body in the first direction, wherein the targeting hole is oriented so that its longitudinal axis is generally oriented toward the rotational axis.

2. The targeting guide of claim 1, wherein the at least one targeting hole is configured to receive a drill guide sleeve or a guide wire.

3. The targeting guide of claim 1, wherein the targeting portion further comprises a second targeting hole provided on the side of the targeting portion that is extending from the body in the first direction, wherein the second targeting hole is also oriented so that its longitudinal axis is parallel to the longitudinal axis of the at least one targeting hole.

4. The targeting guide of claim 3, wherein the second targeting hole is configured to receive a drill guide sleeve or a guide wire.

5. The targeting guide of claim 1, wherein the targeting portion further comprises at least one guide hole spaced apart from the at least one targeting hole and oriented parallel to the at least one targeting hole.

6. The targeting guide of claim 5, wherein the at least one guide hole is configured to receive a guide wire.

7. The targeting guide of claim 1, wherein the at least one guide hole provided in the anchoring portion is oriented so that its longitudinal axis is orthogonal to the rotational axis.

8. The targeting guide of claim 1, wherein the anchoring portion is connected to the body by a swiveling joint configured so that as the anchoring portion swivels, the longitudinal axis of the at least one guide hole stays parallel to a plane defined by the longitudinal axis of the at least one targeting hole as the targeting portion slides along the curved section.

9. The targeting guide of claim 1, wherein the body further comprises a plurality of holes provided between the fulcrum and the curved section, wherein the holes are oriented generally in the first direction, wherein the holes are configured for receiving fixation pins.

10. A method of using a targeting guide for hallux valgus correction procedure, wherein the targeting guide comprising: an anchoring portion comprising at least one guide hole configured for receiving an anchoring element; a targeting portion; a fulcrum; and a body connecting the anchoring portion, the targeting portion, and the fulcrum, wherein, the anchoring portion, the targeting portion, and the fulcrum all extend from the body in a first direction, the fulcrum is located on the body between the anchoring portion and the targeting portion, the body is shaped so that the fulcrum is not in line with the anchoring portion and the targeting portion, the positions of the anchoring portion and the fulcrum on the body are fixed, the body has a curved section whose curvature is defined by a circular arc with a radius of curvature and the targeting portion is slidably connected to the body and is configured to slide along the curved section between a first position and a second position, the radius of curvature has its center located at a point between the anchoring portion and the fulcrum and an axis going through the center of the radius of curvature defines a rotational axis for the targeting portion sliding along the curved section, the targeting portion comprises at least one targeting hole provided on the side of the targeting portion that is extending from the body in the first direction, wherein the targeting hole is oriented so that its longitudinal axis is generally oriented toward the rotational axis, the targeting portion further comprises at least one guide hole spaced apart from the at least one targeting hole and oriented parallel to the at least one targeting hole, the method comprising:
(a) performing an osteotomy cutting a first metatarsal bone into a metatarsal head portion (B2) and a metatarsal base portion;
(b) inserting an anchoring element into the metatarsal head portion from medial side;
(c) slipping the anchoring portion of the targeting guide over the anchoring element;
(d) positioning the targeting guide into a dorsal position by rotating the targeting guide about the anchoring element to determine the location for the fulcrum;
(e) making a stab incision at a location between the metatarsal base portion and a second metatarsal bone where the fulcrum will be inserted;
(f) inserting the fulcrum into the stab incision by further rotating the targeting guide about the anchoring element;
(g) translating the metatarsal head portion in the lateral direction with respect to the metatarsal base portion by pivoting the targeting guide about the fulcrum while bracing the fulcrum against the lateral side of the metatarsal base portion, whereby the anchoring portion urges against the metatarsal head portion;
(h) holding the metatarsal head portion in the translated position by affixing the targeting guide to the metatarsal base portion by placing a fixation pin through a hole that is located in the body between the fulcrum and the curved section;
(i) inserting a first guide wire through the guide hole in the targeting portion; and
(j) adjusting the position of the targeting portion along the curved section until the first guide wire is identifying a desired trajectory for a bone screw to be driven through the metatarsal base portion and into the metatarsal head portion.

11. The method of claim 10, further comprising the step of inserting a drill guide sleeve into the targeting hole in the targeting portion until the drill guide sleeve contacts the patient's skin next to the metatarsal base portion and drilling through the metatarsal base portion and the metatarsal head portion guided by the drill guide sleeve.

12. The method of claim 10, wherein in step (j), identifying the desired trajectory for a bone screw comprises checking the orientation of the first guide wire under a fluoroscope.

13. The method of claim 12, further comprising the step of inserting a drill guide sleeve into the targeting hole in the targeting portion until the drill guide sleeve contacts the patient's skin next to the metatarsal base portion and drilling through the metatarsal base portion and the metatarsal head portion guided by the drill guide sleeve.

14. The method of claim 10, further comprising the step of inserting a drill guide sleeve into the targeting hole in the targeting portion until the drill guide sleeve contacts the patient's skin next to the metatarsal base portion and driving a guide wire through the metatarsal base portion and the metatarsal head portion and using a cannulated drill bit to drill through the metatarsal base portion and the metatarsal head portion guided by the guide wire.

15. The method of claim 12, further comprising the step of inserting a drill guide sleeve into the targeting hole in the targeting portion until the drill guide sleeve contacts the patient's skin next to the metatarsal base portion and driving a guide wire through the metatarsal base portion and the metatarsal head portion and using a cannulated drill bit to drill through the metatarsal base portion and the metatarsal head portion guided by the guide wire.

16. The method of claim 10, wherein in step (b) the anchoring element is inserted into the metatarsal head portion so that the tip of the anchoring element is in the center of the metatarsal head portion.

17. The method of claim 10, wherein after step (i) but before step (j), adjusting the targeting guide's position in dorsal-plantar directions to align the longitudinal axis of the targeting hole to the longitudinal axis of the metatarsal base portion.

18. The method of claim 10, wherein after step (h) but before step (i), adjusting the targeting guide's position in dorsal-plantar directions to align the longitudinal axis of the targeting hole to the longitudinal axis of the metatarsal base portion.

\* \* \* \* \*